United States Patent [19]

Lazarus

[11] Patent Number: 4,551,097
[45] Date of Patent: Nov. 5, 1985

[54] DUAL-TORQUE WINDING AND TIGHTENING TOOL

[76] Inventor: Harry J. Lazarus, 36 Knox La., Englishtown, N.J. 07726

[21] Appl. No.: 702,496

[22] Filed: Feb. 19, 1985

[51] Int. Cl.⁴ .............................................. A61C 5/04
[52] U.S. Cl. ....................................................... 433/39
[58] Field of Search ............................................ 433/39

[56] References Cited

U.S. PATENT DOCUMENTS

| | | |
|---|---|---|
| 3,411,214 | 11/1968 | Lazarus .................................. 433/39 |
| 3,852,884 | 12/1974 | Lazarus .................................. 433/39 |
| 3,921,299 | 11/1975 | Lazarus .................................. 433/39 |

Primary Examiner—Robert Peshock
Attorney, Agent, or Firm—McGlew and Tuttle

[57] ABSTRACT

A dual-torque winding tool for winding a coil of a retainerless dental matrix comprises a handle which can be held and rotated in the hand. A barrel is axially movable within a blind channel defined in the handle, with the handle being rotatable with and over the rotatable barrel. Two separate torque transmitting mechanisms are provided for establishing co-rotation between the handle and the barrel at two separate torque values. In one form of the invention the two separate torque values are established by two spring loaded balls which are under different biasing forces and which each can selectively engage into one of a single set of socket holes. Axial movement of the barrel for bringing one or the other ball into engagement with the socket holes establishes the selected torque value. Another form of the invention uses two separate sets of socket holes each having holes with a different diameter and engageable by a single spring loaded ball.

16 Claims, 12 Drawing Figures

U.S. Patent   Nov. 5, 1985   Sheet 1 of 2   4,551,097
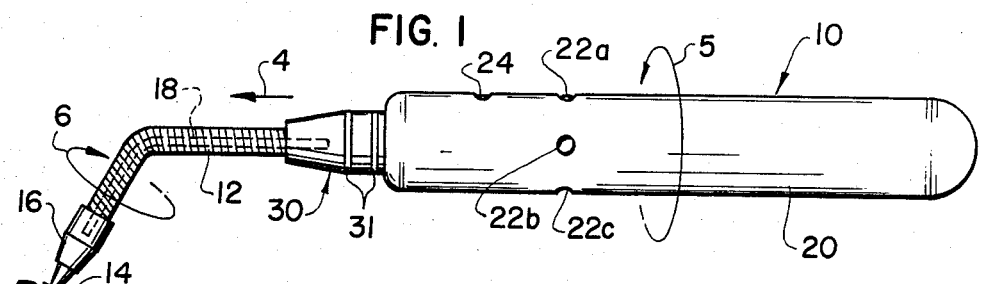
FIG. 1
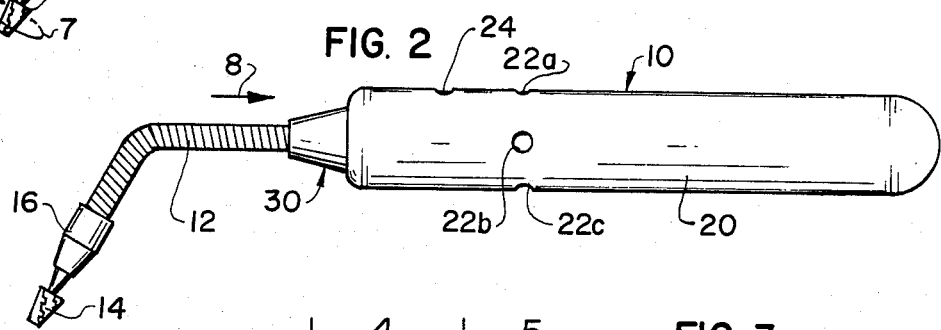
FIG. 2
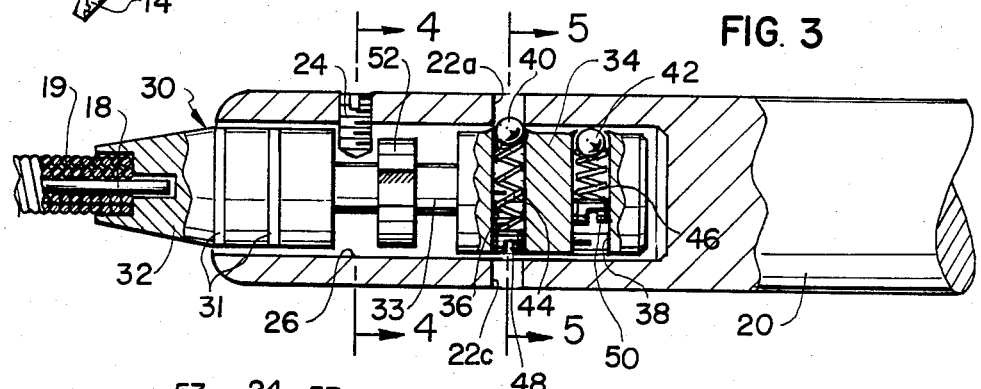
FIG. 3
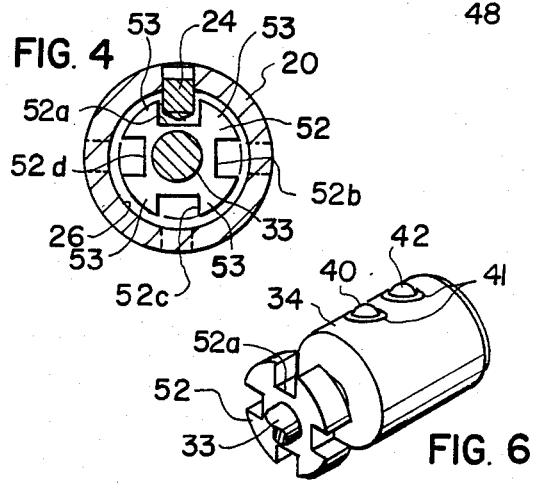
FIG. 4
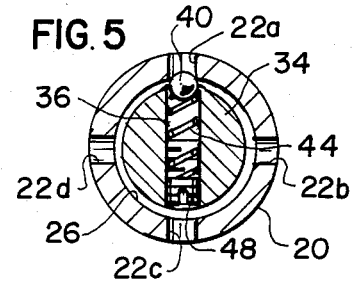
FIG. 5
FIG. 6

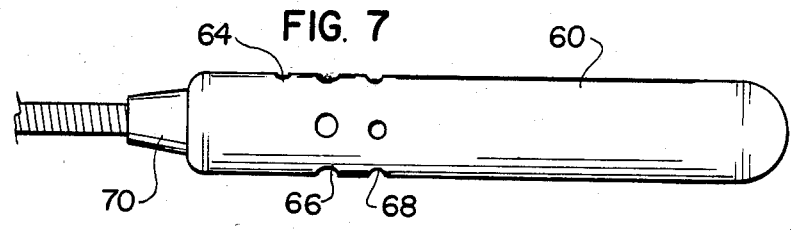
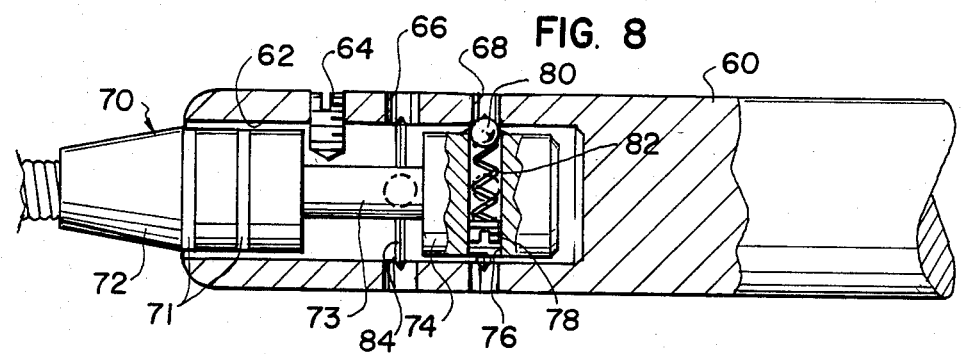
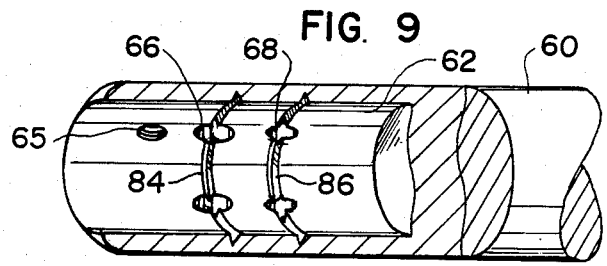
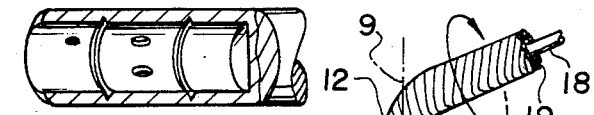
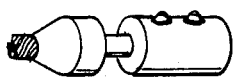
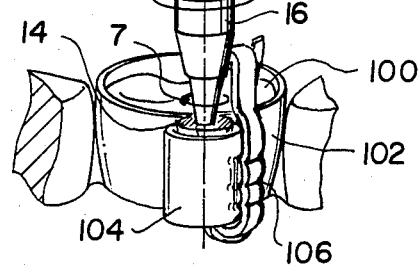

DUAL-TORQUE WINDING AND TIGHTENING TOOL

FIELD AND BACKGROUND OF THE INVENTION

The present invention relates in general to a winding and tightening tool which is used for tightening a preformed coil on a self-locking retainerless dental matrix.

A winding tool of this type was introduced by the present inventor in his previous U.S. Pat. No. 3,435,905 issued Apr. 1, 1969 and entitled TOOL AND METHOD OF MANUFACTURING THE SAME.

Retainerless dental matrices which include a preformed coil and which can be tightened by such a tool are disclosed in the inventor's previous U.S. Pat. Nos. 3,411,214 granted Nov. 19, 1968 and 3,921,299 granted Nov. 25, 1975.

These matrices are made of stainless steel. A selected amount of torque is applied in winding the coil to fully engage and lock the matrix on the tooth. Thereafter, the winding tool is disengaged from the coil and removed from the mouth, thereby, the matrix is locked on said tooth and does not require a retainer to keep it locked thereon, as with other matrices. Retainerless matrices provide greater field of vision and a freer uncluttered operative field for the dentist.

In order to control the required amount of torque, and to avoid applying too much torque to the coil and the matrix itself, and thereby damaging the matrix, the inventor introduced an improvement in his winding tool which is disclosed in U.S. Pat. No. 3,852,884 granted Dec. 10, 1974 and entitled WINDING AND TIGHTENING TOOL AND METHOD OF MANUFACTURING SAME. This winding tool included torque limiting means in the form of spring loaded balls which were engagable in an opening or sockets in the handle for transmitting torque from a handle of the winding tool to the winding member at the tip of the winding tool. When the torque experienced at the winding tip exceeds a selected amount the barrel stops rotating, and the spring loaded ball is depressed by the edge of said rotating socket, thereafter the ball is dislodged from said socket so that torque is no longer conveyed to the barrel or the winding member. In this way excess torque damage to the retainerless dental matrix is avoided, as well as preventing undue torque from being uncomfortably applied to the patient's tooth being restored, as is the case with retainer-type matrices which do not provide torque control.

The present inventor has also disclosed a retainerless dental matrix of the foregoing type which, rather than being made of stainless steel, can be made of plastic. One major advantage of this is that the plastic can be transparent so that light-curable dental restorative materials can be used behind a clear transparent plastic film matrix and set, using said light. The curing light of course can be transmitted through the transparent plastic matrix to cure the material behind the matrix. As with the steel retainerless matrix, this plastic retainerless matrix requires the torque control of this dual torque device of this invention, at a lower torque.

This plastic retainerless dental matrix is disclosed in the inventor's co-pending application having U.S. Ser. No. 586,569, filed Mar. 6, 1984 and now U.S. Pat. No. 4,523,909 issued 6/18/85 entitled PLASTIC DENTAL MATRIX AND METHOD OF MANUFACTURING SAME.

The foregoing patents and patent application to the present inventor are incorporated here by reference.

In developing the plastic dental matrix, the inventor found that several problems had to be overcome which were related to the difference in material strength and other characteristics of plastic as opposed to stainless steel. The inventor also found that a lower amount of torque was necessary for winding the coil of the plastic matrix than the coil of the stainless steel matrix, so as to avoid self destructive tearing of the plastic matrix during use and prior to serving its intended useful purposes, as could occur with high torque.

While the inventor's previous winding tool as disclosed in above identified U.S. Pat. No. 3,852,884, had a mechanism for setting a selected torque, only a single torque setting could be obtained.

SUMMARY OF THE INVENTION

The present invention is drawn to an improved winding and tightening tool for the coil of a retainerless matrix which has at least two torque settings. The lower torque setting can be selected for winding the coil of plastic retainerless dental matrices and the high torque setting can be selected for winding the coil of stainless steel retainerless dental matrices. Thus avoiding the need for tool manufacturers and dentists to stock separate high and low torque tools.

The winding tool of the present invention includes a driving member in the form of a handle which can be held in the hand and rotated. The handle or driving member is rotatably mounted over an internal barrel which can take up at least two separate axial positions in the driving member handle. First and second torque transmitting means are provided for selectively engaging the barrel to the driving member or handle so that torque transmissions up to two separate selected amounts can be transmitted from the handle to the barrel. An internal, non-rotatable angled shaft has a coreless flexible sleeve which is rotatably engaged with said shaft. Said sleeve is connected to the end of said barrel and rotates with rotation of the handle and the barrel. A winding member is connected to the end of the flexible sleeve. The winding member is shaped to engage the interior of a retainerless matrix tightening coil. Said shaft, flexible sleeve, and winding member comprising a shaft means.

According to one form of the invention, the barrel can be placed into two axially spaced locations with respect to the handle. One or more spring loaded steel balls are provided in transverse bores in a portion of the barrel. Where one spring loaded ball is provided, two sets of socket holes are defined in the driving member or handle which are selectively engaged by the steel ball. One set of socket holes is smaller in diameter than the other so that it requires a different or lower amount of torque to dislodge the steel ball from a smaller set of socket holes than from the larger set of socket holes.

In the case where two spring loaded steel balls are provided, each is subjected to a different spring tension and each can selectively be engaged with one set of socket holes for establishing two separate torque settings.

To retain the barrel or barrel assembly in position for either the high or low torque setting in the handle, a position set screw is threaded into the handle and rotatably engages within the bounding or journal surfaces defined as a space in the barrel, of which there are at least one or more such spaces. Alternately, a press-fit pin may be used in place of said position set screw.

To maintain the position of the barrel in either of its high or low torque setting positions, one embodiment of the invention utilizes a slotted escapement disc which permits controlled axial movement of the barrel only through a slot or recessed area of the disc which permits the passage of the position set screw. This axial movement can only be done when the handle is not being rotated. At such time said slot and screw are in axial alignment thus avoiding inadvertent switching of torque settings during use of the tool.

Said axial alignment of the set screw and slot permit axial shifting of the barrel, either inwardly or outwardly for a change from or to high or to a low torque setting, by the pushing or the pulling of the barrel either in or out of the handle. At the time the position set screw passes through the slot, the aligned balls behind the slot, exchange places in their engagement with the handle's socket for a newly set high or low torque.

During rotation of the handle the position set screw is prevented from passing through any of the slots for several reasons: 1. The user's hand action is rotational, not axial, and axial motion is required to pass the position screw through the slot, and, 2. The clearance allowed for said screw to pass through said slot are so minimal that the slightest rotational movement of the screw prevents needed initiation of said axial passage into the slot during use of the tool. To enter the slot, the handle and thus the position screw, must be at a stopped position. Therefore, inadvertent switching of the torque settings does not occur during use of the tool. Torque switching can be accomplished therefore only when the tool is in hand and not when in use intra-orally.

At a rest point, when the tool is not being rotated or being axially repositioned, inadvertent axial movement of the barrel axially cannot occur because while the position set screw is in alignment with the slot, one of the balls is engaged with one of the sockets in the handle with sufficient spring compression to prevent accidental, inadvertent axial movement of the barrel. Unless deliberate user action is taken to force that ball out of that engagement, the torque remains as set.

NOTE:

At one point in use of the tool when the matrix becomes tightened, the barrel will cease to rotate and a slipping action will begin between the barrel and the handle. At that point further torque fails to reach the barrel. A slip clutch type action occurs when said tightened matrix prevents said barrel from rotating, causing the ball-engaging socket to depress the ball and then ride over it, and in the continued rotation of the handle, the next approaching socket engages said ball and likewise it disengages from the same ball for the same reason. These engagements and disengagements result in a sonic clicking, which signals the dentist to stop all rotations as the matrix is now tight.

NOTE:

The switching of the torque setting either from high or low is a two-handed operation, doable out of the mouth only. Intra-oral use of the tool is a one-handed operation which makes intra-oral switching near impossible.

Another embodiment of the invention utilizes circumferentially extending grooves which connect each set of socket holes so that even when a ball is dislodged from a socket hole said ball will continue to ride in a groove to maintain desired respective axial position between the barrel and the handle.

An alternate embodiment to the above said grooves is a pair of circumferentially extending grooves which are axially spaced on opposite sides of said circumferentially spaced sockets, wherein said barrel is provided with said dual spring-loaded balls, one ball provides higher torque than the other to the tool, as shown in FIG. 6. When one ball engages said socket, the other ball rides in the adjacent groove so as to maintain axial positioning of the barrel within the handle during use of the tool. This arrangement is functional regardless of whether the high or low torque ball is engaged with the sockets, or riding in between the sockets. In all instances, inadvertent, accidental shifting of the barrel from one axial torque position to another does not occur.

Accordingly another object of the invention is to provide a dual torque winding tool for winding a coil of a retainerless dental matrix which comprises a driving member or handle adapted to be held and rotated in the hand, which is rotatably mounted on a barrel and having, for example, a low first torque transmitting means engageable between the handle and the barrel for transmitting rotation of the handle to the barrel up to said first selected low torque and second higher torque transmitting means engageable between the handle and the barrel for transmitting rotation of the handle to the barrel up to a second and higher selected torque. Said angled shaft assembly or shaft means are connected to the end of the barrel and terminate with a winding member which is wound with rotation of the barrel, when said handle is rotated.

Another object of the invention is to provide a dual torque winding tool which is simple in design rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a side elevational view of a first embodiment of the winding tool in accordance with the invention shown in a high torque position;

FIG. 2 is a view similar to FIG. 1 showing the tool in a low torque position;

FIG. 3 is a partial sectional view, on an enlarged scale, of the tool shown in FIG. 2;

FIG. 4 is a transverse cross-sectional view taken along the line 4—4 of FIG. 3;

FIG. 5 is a transverse sectional view taken along the line 5—5 of FIG. 3;

FIG. 6 is a partial perspective view of a barrel assembly shown in FIG. 3;

FIG. 7 is a partial side elevational view of a second embodiment of the inventive winding tool;

FIG. 8 is a partial sectional view, on an enlarged scale, of the embodiment of FIG. 7;

FIG. 9 is a perspective interior view of a handle or driving member of the embodiment of FIG. 8, with portions cut away for clarity:

FIG. 10 is a partial perspective view of the winding end of the inventive winding tool engaged with a coil of a retainerless dental matrix;

FIG. 11 is a perspective view of an alternate handle or driving member, with portions cut away for clarity; and FIG. 12 is a perspective view of a barrel assembly of an alternate embodiment functional with the handle of FIG. 11.

DESCRIPTION OF THE PREFERRED EMBODIMENTS

Referring to the drawings in particular, the invention embodied in FIG. 1 comprises a winding tool generally designated 10 for winding the coil of a retainerless dental matrix of the type developed by the inventor of the present application and disclosed in greater detail in the patents set forth above.

As shown in FIG. 10, such a retainerless dental matrix includes a matrix band 102 which can be made of stainless steel or plastic and which can be engaged around a tooth 100 to be treated. Band 102 terminates in a pre-formed winding coil 104 which can be engaged by a winding member or head 14 of the inventive winding tool for rotation in a clockwise direction as shown by arrow 7. This rotation draws additional material of band 102 under a retaining lock-loop 106 and onto coil 104, thereby enlarging the diameter of the coil. This causes a locking effect under lock-loop 106. This locking effect is maximized at a certain torque value which is reached when the matrix is fully tightened and resists further tool rotation. Beyond this point, further rotation of the handle no longer further tightens the coil, or the matrix on the tooth. The matrix is tight. It is thus desirable to end further rotation of head 14 beyond this selected torque value, as further, uncontrolled, increased torque would tear the matrix from its engagement with the lock-loop and render the matrix useless prior to having served its useful purpose of containing the restorative materials.

It is also noted that the selected torque value in a torque controlled tool is higher for a stainless steel band than for a plastic band, as high torque would tear the plastic matrix.

Turning once more to FIG. 1, tool 10 includes a driving member or handle 20 which rotatably receives a barrel or barrel assembly 30. Barrel assembly is shown in an "out", high torque position, having been telescopically pulled out fully from the handle by a dentist in the direction of arrow 4.

Also shown in FIG. 1 is said angled shaft assembly 12 which is capable of transmitting rotation of barrel 30 to rotation of a socket chuck 16. Socket chuck 16 is connected for co-rotation with winding member 14.

Shaft assembly 12 includes an outer hollow sleeve 19 made for example of coiled wires, and an inner non-rotatable pre-angled shaft or core 18, which lies freely within the hollow of said sleeve 19.

Rotation of handle 20 in the direction of arrow 5 causes rotation of sleeve 19 in the direction of arrow 6 and thus the rotation of winding member or head 14 in the direction of arrow 7.

While this effect is fully covered in the above identified patent, it will be reviewed briefly in connection with FIG. 10.

As shown in FIG. 10, the angled core or shaft 18 extends into the flexible sleeve 19 which is made of an inner wire coiled in one helical direction in a spaced manner around shaft 18, and a second outer wire coiled in an opposite helical direction. Elements 18 and 19 form the angled shaft 12.

The wires of flexible, hollow sleeve 19 are firmly connected to the socket chuck 16 and the socket chuck 16 in turn is firmly connected to the winding head 14.

The winding head and chuck are kept in axial alignment on a winding axis 9 by virtue of the fact that head 14 is inserted into the center of coil 104. This results in the fact that even with rotation in the directions of arrows 6 and 7, the winding head will not leave the axis 9 but rather will rotate within the coil 104. Shaft or core 18, which does not rotate, has a bent area which maintains the angled shape of flexible shafting sleeve 19 as this sleeve is rotated.

FIG. 2 shows a low torque position for the winding tool 10. To select this low torque position a dentist has pushed barrel assembly 30 deeper fully into handle 20 in the direction of arrow 8. Conversely the outer-most position of the barrel sets the tool in a high torque mode.

FIGS. 3 through 6 show details of the dual torque escape mechanism for establishing the two selected torque values.

As shown in FIG. 3, driving member or handle 20 includes a blind central channel 26 which is rotatably engaged over assembly 30. Handle 20 includes one set of four socket holes 22a through 22d (FIG. 5). As will be explained later, during use of the tool, one of these socket tools is engaged by a steel ball 40 which establishes engagement between the barrel assembly 30 and the handle 20 so that rotation of the handle is transmitted, with a selected torque value, to the barrel 30.

Handle 20 also includes a threaded bore which threadably receives a position set screw 24 for establishing two separate axial positions for barrel 30.

Barrel 30 includes a forward portion 32 which is connected to the flexible sleeve 19 and which loosely receives the core shaft 18. Front portion 32 carries position indicating means in the form of two circular indicating stripes 31.

Barrel 30 also includes a rear portion 34 which is connected to the front portion 32 by a connecting shaft 33.

Rear portion 34 includes two transverse through bores 36 and 38 which each have threaded ends and threadably receive set screws 48 and 50.

Set screws 48 and 50 respectively bear against springs 44 and 46 which respectively engage steel balls 40 and 42.

In the position shown in FIG. 3, ball 44 which is subject to relatively low tension by compression spring 44 establishes a low torque setting by engaging one of the socket holes 22a. With rotation of handle 20 beyond this selected torque value, socket 22a will disengage from ball 40. The dentist then can continue rotating handle 20 but no rotation will be transmitted to barrel 30 and the barrel stops rotating. Thereafter, a clicking sound results however as non-rotating barrel ball 40 is engaged and disengaged subsequently in handle revolving socket holes 22b, 22c and 22d. This produces a sonic indication to the dentist that the selected torque has been reached and no more winding is necessary.

Ball 42, its spring 46 and set screw 50 operate in exactly the same fashion with the difference being that compression spring 46 is under greater tension and thus exerts more force on ball 42. In this way, when barrel 30 is pulled out of handle 20 in the direction of arrow 4

(FIG. 1) steel ball 42 will engage one of the socket holes, which transforms the tool thereby from low torque to high torque tool.

By the use of two spring loaded balls, two separate torque transmitting means are established for transmitting torque from the handle to the barrel. It should be noted that the provision of three or more spring loaded balls on said barrel would in turn provide the tool with multitorque capacity.

In order to maintain the correct axial position of barrel 30 with respect to handle 20, when the barrel stops rotating and no ball is engaged, with any of the socket holes in the rotating handle the barrel is provided with an escapement disc 52 which is fixed on connecting shaft 33.

As shown in FIG. 4, escapement disc 52 includes four circumferentially spaced slots 52a, 52b, 52c and 52d. As shown in FIG. 6, one of these slots (52a) is axially aligned with the balls 40 and 42.

As shown in FIG. 4, for the purpose of switching from one torque setting to another, each slot 52a through 52d is sufficiently deep and wide to permit the relative axial movement between escapement disc 52 (of the connected barrel assembly 30) and the position set screw 24, in the handle.

While set screw 24 is in alignment with one of the slots 52a through 52d, and the handle is not being rotated the axial position of barrel 30 is maintained by virtue of the fact that one of the balls is engaged with one of the socket holes, unless deliberate axial movement of the barrel is made to change from one torque setting to the other. Axial barrel movement is not possible when the handle is being rotated.

When one of the two selected torques has been reached during rotational use of the tool and a socket hole disengages from one of the balls, the continued rotation of the handle 20 and the non-rotating barrel 30, causes one of the web areas 53 of escapement disc 52, between the slots 52a through 52d, to become axially aligned with the position set screw 24, thereby holding the non-rotating barrel 30 in its pre-set axial position. While the handle 20 continues to be rotated, without permitting inadvertent switching from one torque setting to another, which can only be switched when the handle is not being rotated, and a ball is engaged with a socket which occurs automatically when the user stops winding the tool.

It is noted that the extreme ends of the two opposite axial positions which can be taken up by barrel 30 are established by facing radial walls of front portion 32 and rear portion 34.

As also shown in FIG. 6, balls 40 and 42 can be retained in their respective bores by peen areas 41. This is provided for ease of assembly but is not necessary.

FIG. 5 shows the position of low torque ball 40, spring 44 and set screw 48. Ball 40 is shown engaged in socket hole 22a.

While relatively large clearances are shown between the barrel 30 and the blind channel 26 of handle 20, in an actual device, these clearances are much smaller. The clearances have been illustrated for clarity in the drawings.

FIGS. 7 through 9 show a second embodiment of the invention wherein the first and second torque transmitting means are formed at least partly by two sets of socket holes 66 and 68. Each set of socket holes includes one or more holes which are circumferentially aligned around handle 60.

As with the embodiment of FIG. 1, a set screw 64 is provided for establishing two distinct axial positions between a barrel or barrel assembly 70 and the handle 60.

Two separate torque settings are established by the fact that the diameter of socket holes 66 is larger than the diameter of socket holes 68. In a preferred form of the invention, socket holes 66 may have a diameter of about 0.1 inches for high torque while socket holes 68 have a diameter of about 0.06 inches, for low torque (said dimensions serve only as examples).

Barrel 70 comprises a front portion 72 and a rear portion 74 connected thereto by a connecting shaft 73.

Rear portion includes a transverse bore 76 which threadably receives a set screw 78 which bears against a compression spring 82 for applying a selected force on steel ball 80. In the position shown in FIG. 8, steel ball 80 engages one of the small diameter socket holes 68 for establishing a low torque position. This is because it is easier for small diameter socket holes 68 to depress ball 80, and disengage the hole from the ball than it would be to depress ball 80 and disengage it from the larger diameter socket holes 66. Both socket holes must have a diameter which is less than the diameter of the ball 80 however.

FIG. 9 shows an alternate form for an axial position maintaining means for maintaining the two selected axial positions of barrel 70. Rather than utilizing an escapement disc as in the embodiment of FIGS. 1 through 6, the embodiment of FIGS. 7 through 9 utilize circular grooves 84 and 86 which communicate with the respective sets of socket holes 66 and 68. In this way, even when ball 80 leaves one of the socket holes, it still rides in one of the grooves 84 or 86, thus maintaining the high or low torque position for barrel 70.

As with the embodiment of FIG. 1, indicating stripes 71 are defined on front portion 72 for providing a clear visual indication to the dentist, on which position is being utilized.

FIG. 11 is a view similar to FIG. 9 but showing an alternate embodiment including two spaced apart circumferential grooves which have a circumferentially distributed row of sockets therebetween. The handle of FIG. 11 can be used with the barrel of FIG. 12. The barrel of FIG. 12 is similar to that of the embodiment of FIG. 3 in that two spring loaded balls are utilized, one being under a greater tension than the other. In this way one of the balls is always engaged with one of the grooves of FIG. 11 while the other ball is associated with the row sockets. No escapement is necessary since an annular space is provided in the barrel of FIG. 12 which cooperates with a position set screw of the handle (not shown in FIG. 11).

It is noted that in all embodiments of the invention, the position with the barrel out (thereby showing stripes 31 or 71) corresponds to a high torque position. This is because it is more difficult, in the high torque position, for the barrel to be inadvertently pushed inwardly to the other setting. The "in" setting in all embodiments corresponds to the low torque position since little or no further inward axial movement is possible for the barrel 30 or 70 by virtue of the fact that blind channel 26 or 62 are provided to be only slightly longer than necessary to fully accommodate their respective barrel.

While specifc embodiments of the invention have been shown and described in detail to illustrate the application of the principles of the invention, it will be understood that the invention may be embodied otherwise without departing from such principles.

What is claimed is:

1. A dual-torque winding tool for winding a coil of a retainerless dental matrix, comprising:
a handle adapted to be held and rotated in a hand;
a barrel over which said handle is rotatably mounted;
first torque transmitting means engageable between said handle and said barrel for transmitting rotation of said handle to said barrel up to a first selected torque;
second torque transmitting means engageable between said handle and said barrel for transmitting rotation of said handle to said barrel up to a second selected torque which is different from said first selected torque;
angled shaft assembly means connected to said barrel, and angled shaft means having a first end connected to said barrel and a second end remote from said barrel, said first and second ends of said angled shaft means being rotatable with rotation of said barrel; and
a winding head connected to said second end of said angled shaft assembly means adapted for engaging and winding a coil of a retainerless dental matrix.

2. A winding tool according to claim 1, wherein said barrel is movable into a first and a second axial position with respect to said handle, said first torque transmitting means being engaged between said handle and said barrel with said barrel in said first axial position and said second torque transmitting means being engaged between said handle and said barrel with said barrel in said second axial position, and including axial position maintaining means engaged between said handle and said barrel for maintaining said barrel in said first and second axial position thereof.

3. A winding tool according to claim 2, wherein said handle includes a blind channel defined therein, said barrel rotatable and axially movable in said channel, said axial position maintaining means comprising said barrel having a front portion and a rear portion connected to said front portion and defining a circumferential space therebetween, and a position set member connected to said handle and extending into said space, said first axial position established with said front portion substantially engaging said position set member and said second axial position established with said rear portion substantially engaging said position set member.

4. A winding tool according to claim 3, including a connecting shaft connected between said front and rear portions, said axial position maintaining means including an escapement connected to said shaft and dividing said space into a front area and a rear area, said position set means being in said front area with said barrel in its first axial position and being in said rear area with said barrel in its second axial position, said escapement including at least one slot therethrough for permitting said position set means to move between said front and rear areas.

5. A winding tool according to claim 4, wherein said first torque transmitting means comprises a first bore in said rear portion of said barrel, a first ball movable in said first bore, a first spring engaged in said first bore and against said first ball and a first torque set screw engaged in said first bore and against said first spring to hold said first spring against said first ball at a selected biasing force for establishing said first selected torque, said second torque transmitting means comprising a second bore in said rear portion axially spaced from said first bore, a second ball in said second bore, a second spring in said second bore engaged against said second ball, and a second torque set screw engaged in said second bore and against said second spring for exerting a second biasing force on said second ball for establishing said second selected torque, said handle including at least one socket hole therethrough engageable with one of said first and second balls with said barrel in its first and second axial position respectively.

6. A winding tool according to claim 5, wherein said first torque set screw is positioned to exert less force on said first ball than said second torque set screw, said first bore being closer to said front portion than said second bore so that said first axial position is established with said barrel deeper into said channel than said second axial position, said first selected torque being lower than said second selected torque.

7. A winding tool according to claim 6, wherein said angled shaft means comprises a flexible sleeve connected from said first to said second end of said angle shaft means, a nonrotating pre-angled shaft in said flexible sleeve and a socket chuck connected to said sleeve at said second end of said angled shaft means, said winding member connected to said socket chuck.

8. A winding tool according to claim 7, including at least one indicating stripe on said front portion which is positioned out of said handle channel with said barrel in its second axial position, and is covered by and disposed in said channel with said barrel in its first axial position.

9. A winding tool according to claim 3, wherein said first torque transmitting means comprises at least one first socket hole in said handle communicating with said channel, said second torque transmitting means comprising at least one second socket hole in said handle communicating with said channel at an axially spaced location from said first socket hole and having a different diameter from a diameter of said first socket hole, said rear portion of said barrel having a bore therein, a ball in said bore, a spring in said bore engaged against said ball for exerting a force on said ball and a torque set screw in said bore engaged against said spring for establishing said force, said ball engaged with said first socket hole with said barrel and said first axial position and with said second socket hole with said barrel and second axial position.

10. A winding tool according to claim 9, wherein said axial position maintaining means comprises a first circular groove extending in said channel and communicating with said first socket hole and a second circular groove extending in said channel and communicating with said second socket hole.

11. A winding tool according to claim 10, wherein said angled shaft means comprises a flexible sleeve connected from said first to said second end of said angled shaft means, a non-rotating pre-angled core in said flexible sleeve and a socket chuck connected to said sleeve at said second end of said angled shaft means, said winding member connected to said socket chuck.

12. A winding tool according to claim 3, wherein said first torque transmitting means comprises a first bore in said rear portion, a first ball movable in said first bore, a first spring engaged in said first bore and against said first ball and a first torque set screw engaged in said first bore and against said first spring to hold said first spring against said first ball at a selected biasing force for establishing said first selected torque, said second torque transmitting means comprising a second bore in said rear portion axially spaced from said first bore, a second ball in said second bore, a second spring in said second bore engaged against said second ball, and a second torque set screw engaged in said second bore and against said second spring for exerting a second biasing forced on said second ball for establishing said second selected torque, said handle including at least one socket hole therethrough engageable with one of said first and second balls with said barrel in its first and second axial position respectively.

13. A winding tool according to claim 1, wherein said angled shaft means comprises a flexible sleeve connected from said first to said second end of said angled shaft means, a nonrotating pre-angled core in said flexible sleeve and a socket chuck connected to said sleeve at said second end of said angled shaft means, said winding member connected to said socket chuck.

14. A winding tool according to claim 4, wherein said angled shaft means comprises a flexible sleeve connected from said first to said second end of said angled shaft means, a nonrotating pre-angled core in said flexible sleeve and a socket chuck connected to said sleeve at said second end of said angled shaft means, said winding member connected to said socket chuck.

15. A winding tool according to claim 2, wherein said first and second torque transmitting means each include sonic means for emitting a sonic signal when said respective first and second selected torques have been reached and said handle rotates with respect to said barrel.

16. A winding tool according to claim 3, wherein said first torque transmitting means comprises a first bore in said rear portion, a first ball movable in said first bore, first biasing means in said first bore for exerting a biasing force on said first ball, said second torque transmitting means comprising a second bore in said rear portion axially spaced from said first bore, a second ball in said second bore and second biasing means in said second bore for exerting a biasing force against said second ball, said handle including at least one socket hole therethrough engageable with one of said first and second balls with said barrel in its first and second axial position respectively, and said handle including a pair of axially spaced annular grooves positioned on opposite sides of said at least one socket with one of said first and second balls being engaged with one of said grooves with the other of said first and second balls being engaged with said socket.

* * * * *